(12) United States Patent
Dunne et al.

(10) Patent No.: US 6,626,834 B2
(45) Date of Patent: Sep. 30, 2003

(54) SPIRAL SCANNER WITH ELECTRONIC CONTROL

(76) Inventors: Shane Dunne, 95 Michael Grass Cresent, Kingston (CA), K7M 2W2; Steven Charles, 3220 Oak Manor Dr., Germantown, TN (US) 38138

( * ) Notice: Subject to any disclaimer, the term of this patent is extended or adjusted under 35 U.S.C. 154(b) by 210 days.

(21) Appl. No.: 09/768,821

(22) Filed: Jan. 25, 2001

(65) Prior Publication Data

US 2002/0143252 A1 Oct. 3, 2002

(51) Int. Cl.[7] .................................................. A61B 8/00
(52) U.S. Cl. ...................................... 600/444; 244/3.16
(58) Field of Search .................................. 600/444, 407, 600/446, 437, 445, 447, 459, 462–467; 73/633; 361/152–154; 359/198–199, 212–213, 202; 244/3.16

(56) References Cited

U.S. PATENT DOCUMENTS

| | | | |
|---|---|---|---|
| 4,092,867 A | 6/1978 | Matzuk | |
| 4,277,039 A | 7/1981 | Blanning et al. | |
| 4,732,156 A | 3/1988 | Nakamura | |
| 4,973,013 A | 11/1990 | Klaus, Jr. | |
| 5,064,285 A | 11/1991 | Iddan | |
| 5,159,931 A | 11/1992 | Pini | |
| 5,357,963 A | 10/1994 | Mayol et al. | |
| 5,454,371 A | 10/1995 | Fenster et al. | |
| 5,562,095 A | 10/1996 | Downey et al. | |
| 5,647,367 A | 7/1997 | Lum et al. | |
| 5,691,834 A | * 11/1997 | Plesko | ........................ 359/202 |
| 5,701,901 A | 12/1997 | Lum et al. | |
| 5,779,187 A | 7/1998 | Dulat et al. | |
| 5,842,473 A | 12/1998 | Fenster et al. | |
| 5,870,219 A | * 2/1999 | Plesko | ........................ 359/199 |
| 5,964,707 A | 10/1999 | Fenster et al. | |
| 6,198,956 B1 | 3/2001 | Dunne | |

FOREIGN PATENT DOCUMENTS

| | | |
|---|---|---|
| CA | 2254939 | 10/1998 |
| CA | 2261227 | 1/1999 |

* cited by examiner

Primary Examiner—Quang T. Van
(74) Attorney, Agent, or Firm—Marks & Clerk

(57) ABSTRACT

A scanning device, typically ultrasonic, can make a volumetric scan of a conical scanning field. A transducer having a permanent magnet at its back end is gimbal mounted in a housing. Behind the permanent magnet is a hemispheric electromagnet coil assembly having at least two wound electromagnet coils. The coils are energized in turn with an alternating current signal, with the signal applied to any coil being out of phase with the signal applied to any other coil by $180°/n$, where n is the number of coils in the hemispheric electromagnet coil assembly. Volumetric scanning is possible by periodically modulating the magnitude or frequency of the signals applied to the coils.

14 Claims, 5 Drawing Sheets

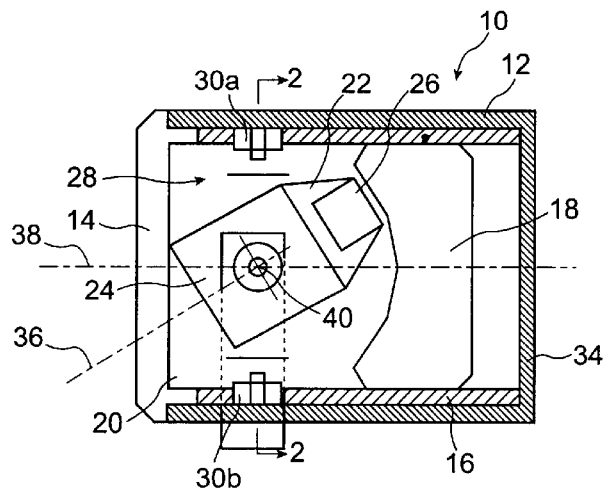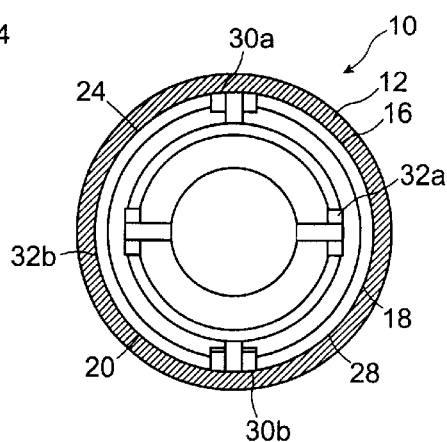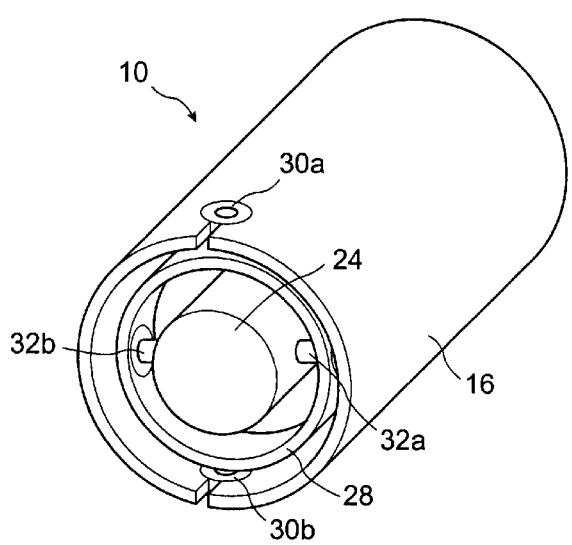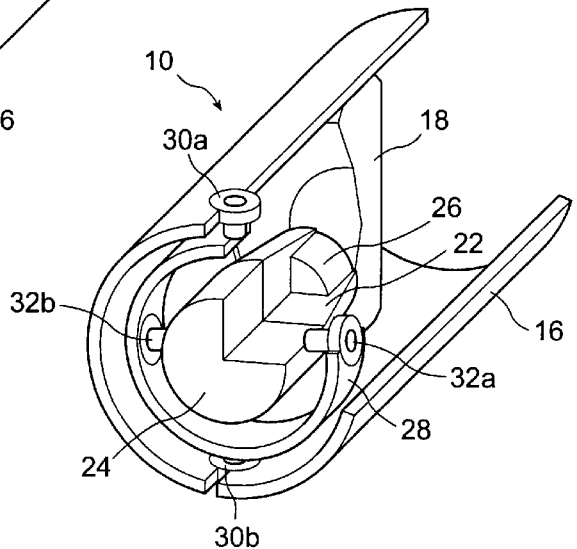
Figure 1
Figure 2
Figure 3
Figure 4

SPIRAL SCANNER WITH ELECTRONIC CONTROL

FIELD OF THE INVENTION

This invention relates to scanning devices whereby a target within a conical scanning field may be scanned so as to obtain a three dimensional scanned image. The target is spirally scanned. The invention also provides for volumetric scanning of a target within the conical scanning field. The invention is particularly directed towards ultrasonic scanners, but optical scanners are also contemplated.

BRIEF DISCUSSION OF THE INVENTION

Typically, the present invention is directed to an ultrasonic scanning apparatus wherein an ultrasonic transducer is mounted for continuous rotation about a pivot point, with motive force provided by electromagnetic means under digital electronic control. Preferably, a scanning apparatus in keeping with the present invention employs a transducer assembly which is disposed within a hand-held probe.

Briefly, such an ultrasonic scanner has a housing, and an ultrasonic transducer disposed within the housing and mounted therein for two-way tilt motion about a pivot point by means of a gimbal or similar mechanism. A permanent magnet is affixed to the rear of the transducer, and electromagnetic means are provided to effect movement of the transducer/magnet assembly. The electromagnetic means comprises at least two electromagnet coils which jointly form a hemispheric electromagnet coil assembly. The electromagnetic coils are driven by polyphase sinusoidal electric currents, causing rotation of the transducer about an axis. Periodic amplitude variation of the polyphase electric currents will effect periodic change of the angle between the axis and a fixed central axis, thereby causing the ultrasonic beam to sweep out a conical volume—and thereby resulting in volumetric scanning.

Electrical means are provided for energizing the transducer and receiving signals therefrom which are indicative of reflected scanning energy which is reflected back from a target in the conical scanning field. Digitizing means are provided to convert the received signals to digital form for storage and/or display.

Sequential control means are provided to energize the electromagnet coils with precise phasing, and further more to synchronize transducer motion, periodic energization of the transducer, and digitization of signals received from the transducer. Of course, suitable storage and/or display means are provided to store and/or to present the signals received by the transducer to an operator, in any one of several time-varying graphical representations.

In an extension of the present invention, the transducer may be replaced by a mirror, with an external light source being arranged to direct light onto the mirror from whence it will be re-directed and transmitted linearly outwardly therefrom.

PRIOR ART CONSIDERED HEREIN

The following is a list of issued United States patents and Published Canadian Patent Applications which are referred to hereafter:

| | | |
|---|---|---|
| U.S. Pat. No. 4,092,867 | issued Jun. 6, 1978 | MATZUK |
| U.S. Pat. No. 4,732,156 | issued Mar. 22, 1988 | NAKAMURA |
| U.S. Pat. No. 5,159,931 | issued Nov. 3, 1992 | PINI |
| U.S. Pat. No. 5,357,963 | issued Oct. 25, 1994 | MAYOL et al |
| U.S. Pat. No. 5,454,371 | issued Oct. 3, 1995 | FENSTER et al |
| U.S. Pat. No. 5,562,095 | issued Oct. 8, 1996 | DOWNEY et al |
| U.S. Pat. No. 5,647,367 | issued Jul. 15, 1997 | LUM et al |
| U.S. Pat. No. 5,701,901 | issued Dec. 30, 1997 | LUM et al |
| U.S. Pat. No. 5,842,473 | issued Dec. 1, 1998 | FENSTER et al |
| U.S. Pat. No. 5,964,707 | issued Oct. 12, 1999 | FENSTER et al |
| U.S. Pat. No. "unknown" | to issue from Ser. No. 09/409,095-now allowed | DUNNE |
| CAPTA 2,261,227 | filed Jun. 25, 1998- laid open Jan. 7, 1999 | FENSTER et al |
| CAPTA 2,254,939 | filed Mar. 20, 1998- laid open Oct. 1, 1998 | FENSTER et al |

BACKGROUND OF THE INVENTION

Ultrasonic imaging, also called echography or B-mode ("brightness mode") ultrasound, involves an ultrasonic transducer which repeatedly emits pulses of high-frequency sound and receives the resulting echo signals. A focused beam of sound is normally used, and various means are employed to sweep this beam repeatedly through a range of directions. Electronic processing of the received echo signals, synchronized to the movement of the beam, results in formation of a video image (normally cross-sectional) of structures (such as human tissues) in the beam's path.

For purposes of clarity, the following discussion refers specifically to the medical diagnostic imaging situation in which the target of the ultrasonic imaging system is tissue in a living human patient. It should be realized that ultrasonic scanning is also used in other applications including non-human (veterinary or in vitro tissue sample) biological imaging and also non-biological imaging applications (non-destructive materials testing), and that the present invention applies without limitation to all of such ultrasonic imaging applications.

In ultrasonic scanners for medical diagnostic imaging, the transducer and beam-sweeping components are normally assembled in the form of a hand-held probe connected to the rest of the imaging system by means of a cable. In the following discussion, the term "probe" will be used generically to refer to the transducer and beam-scanning assembly, though it should be realized that not all ultrasonic scanning systems will have or need a physically distinct probe component.

Historically, B-mode ultrasound imaging has been a two-dimensional process. The sweep motion of the sound beam emitted and received by the transducer is confined to a single plane intersecting the target to be imaged, and a cross-sectional image results. U.S. Pat. Nos. 5,159,931, 5,454,371, 5,562,095, 5,842,473, and 5,964,707 describe methods by which three-dimensional images may be assembled from multiple planar echographic images. However, it is also possible to reconstruct three-dimensional images directly, by causing the transducer to move with two degrees of freedom, with the result that the sound beam sweeps throughout the target volume in some predetermined (programmed) path. The present invention relates to this latter approach, and is referred to as volumetric scanning.

Many techniques for sweeping the sound beam are known; U.S. Pat. No. 4,092,867 presents a good summary. Today, two main approaches are in common use. In the mechanical sector-scan approach, a transducer is mechanically oscillated about a pivot axis, causing the sound beam to sweep through a sector. In the electronic transducer array approach, a fixed array of multiple transducer elements is used, and the sound beam is formed, focused, and swept entirely electronically.

Attempts to use the electronic array approach for volumetric scanning, using a two-dimensional array of transducer elements, have not yet proved practical, and in any event the cost and complexity of the electronics to process the hundreds of individual element signals which would be required are formidable. In contrast, the simple mechanical sector-scan approach can in principle be adapted for volumetric scanning by permitting the transducer to oscillate about a pivot point rather than a pivot axis, e.g. using a gimbal or similar mechanism.

Any number of sweep paths may be envisaged, and if the electronic array approach is used almost any path might reasonably be used to effectively scan a target volume at high speed. With mechanical scanning, however, the only practical sweep path is a circular spiral. Non-spiral paths require rapid changes of the acceleration vector, which in practice will greatly limit the operating speed. Rapid scanning is desirable because it permits dynamic imaging in the presence of motion, e.g. of the living fetus in utero, of the tissues in the eye, or in the course of interventional medical procedures such as catheterization or laparoscopic surgery. The present invention relates to mechanical, spiral scanning of a single transducer mounted for motion with two degrees of freedom in e.g. a gimbal.

Because the sound frequencies used in ultrasonic imaging are effectively blocked by air, it is necessary to acoustically couple the transducer to the target under investigation via one or more acoustically conductive media. Coupling media must be chosen carefully, to ensure that the effects of sound reflection and refraction occurring at media interfaces does not unduly compromise the imaging capabilities of the system. In practice, the problem of coupling is addressed in one of three ways:

1. Liquid bath. Transducer and target are immersed in a liquid coupling medium such as water or sterile saline solution. This technique is rarely used in clinical scanning applications.
2. Sealed transducer chamber. The transducer is sealed within a liquid-filled chamber within the probe, with a solid "acoustic window" through which the imaging beam can pass.
3. Acoustic coupling gel. Several water-based gel media are now on the market, which provide a convenient means to couple a probe's acoustic window to the surface of target tissue.

In any mechanical scanning approach, acoustic coupling to target tissue may be achieved either by method 1 above, or more commonly, a combination of methods 2 and 3. The present invention also discloses some specialized variations of methods 2 and 3.

So-called annular array transducers, which consist of a small number of concentric ring-shaped transduction elements, may be used in place of a single-element transducers in a mechanical sector scanning apparatus. These devices permit electronic control of sound beam focusing, but not direction. Because the number of transduction elements is small (e.g. three to eight), the cost premium associated with annular array transducers is slight compared with that of a full electronic array beam sweeping system. In this application, the term "transducer" refers equally to either a single element transducer or an annular array transducer.

Motive force in mechanical sector scanning devices frequently involves use of an ordinary rotating electric motor plus some form of mechanical linkage to transform rotational motion to back-and-forth oscillatory motion of the transducer. U.S. Pat. No. 5,357,963 discloses a variation of the standard linkage in which the force of attraction between two permanent magnets is used to effect transfer of motive force through the wall of a sealed fluid-filled transducer chamber. U.S. Pat. No. 4,732,156 discloses a similar concept in which the sealed transducer chamber and magnetic linkage are disposed at the end of a flexible mechanical coupling shaft to facilitate insertion of the whole assembly into a body cavity, and the sound beam from a fixed transducer is caused to scan by means of a rotating mirror.

Purely mechanical means of oscillation, with or without use of magnetic elements on some of the moving members to transfer force across a gap, exhibit a number of disadvantages. The mechanical drive assembly adds substantially to the size and weight of the imaging probe, and to achieve precisely controlled motion it is necessary to augment the mechanical system with a positional sensor and to employ closed-loop feedback control methods in the control system. Addition of the positional sensor adds yet further to the size, weight, and complexity of the probe, while the need for closed loop feedback control adds to the complexity of the control system.

U.S. Pat. No. 4,092,867 discloses two mechanisms in which motive force is applied by means of magnetic forces established between fixed electromagnets, energized with time-varying electric current, and a single permanent magnet affixed to a rotating transducer assembly. U.S. Pat. Nos. 5,647,367 and 5,701,901 describe broadly similar mechanisms suitable for micro-fabrication. In all of these cases, the magnetic oscillator mechanism follows the general principle of a galvanometer, i.e., a magnetic field is established in a fixed stator member, with the magnetization vector substantially at right angles to that of a permanent magnet affixed to a pivoted rocker member. The magnet in the rocker is thus subjected to magnetic torque forces which cause it, and the rocker, to tilt or rotate so as to reduce the angle between the two magnetic vectors. Periodically reversing the direction of the stator field, by passing an alternating current through the one or more electromagnet coils in the stator assembly, thus results in a periodically reversing torque applied to the rocker, and in consequence causes the rocker to oscillate.

In practice, such galvanometer-like mechanisms cannot transfer appreciable amounts of mechanical energy, because of the inverse square relationship between magnetic force and distance. As the rocker magnet tilts away from the center position, it moves further from the stator magnet poles, dramatically reducing the torque efficiency of the system and making it harder to apply the reverse torque required to tilt the rocker back in the opposite direction. Such a system is rather like a heavy weight balanced atop a rod held in the hand; provided the rod does not tip very far from the vertical, small movements of the hand suffice to keep it stably aloft, but the range of controllable motion is very small. U.S. Pat. No. 4,092,867 explicitly acknowledges the need for an active feedback control system to maintain stable motion, while U.S. Pat. Nos. 5,647,367 and 5,701,901 address the problem in a limited way by proposing a specially fabricated rocker of near-zero mass driven by a stator electromagnet of enormous relative size. In both cases the result is a probe mechanism substantially larger than the size of the ultrasonic transducer itself.

U.S. Pat. No. "unknown" (to issue from Ser. No. 09/409, 095) discloses an invention which addresses the torque efficiency problems by using a system of many digitally switched stator electromagnet coils, which permit periodic alteration of the magnetic field vector while maintaining a small and little-varying gap between the currently active stator poles and a permanent magnet in the rocker; and furthermore solves the problem of stability at higher operating speeds by providing additional permanent magnets affixed to the stator near the extremes of the rocker's oscillatory motion, oriented so as to repel the permanent magnet in the rocker, causing it to spring back in the opposite direction.

In all of these cases, the most difficult problem to overcome is the need for periodic reversal of the force applied to the transducer, in order to effect back-and-forth motion. A spiral-scan approach sidesteps this problem, however. Circular motion can be effected by means of a continuously-rotating, centrally-directed (centripetal) force vector; gradually increasing and decreasing the magnitude of this rotating vector results in spiral motion. In the present invention, this is accomplished using electromagnetic means.

Reconstruction of an ultrasound image requires means to correctly locate each image point within the visual display. In a modern digital imaging system, the display is usually formed using a raster-scan system comprising a regular, Cartesian-coordinate grid of discrete points or pixels, whereas the acquisition of image points occurs, due to sector scanning, on some form of Polar-coordinate grid. Image reconstruction is hence a coordinate transformation process which is amenable to digital implementation using a fixed coordinate lookup table. With spiral volumetric scanning as in the present invention, image data points are most naturally defined on a spherical-coordinate grid, and there is the added problem that while image data are acquired throughout a three-dimensional (conical) volume, they must somehow be displayed on a two-dimensional surface, e.g. that of a cathode-ray tube or flat-panel display.

Image reconstruction cannot be performed with any fidelity unless the precise geometric location of each acquired image point is accurately known. In a practical continuous-sweep imaging system, this is essentially a matter of proper synchronization of the mechanical and electronic apparatus. Historically, various means of instrumenting the physical motion of a transducer have been used to provide a feedback signal to be used in a closed-loop synchronization system. With electronic array scanning techniques, there is no physical motion and hence the problem is greatly simplified; no feedback is required. U.S. Patent No. "unknown" (to issue from Ser. No. 09/409,095) discloses a mechanical sector-scanning apparatus in which motive force is provided by a system of digitally switched electromagnets acting upon a permanent magnet affixed to the rear of a pivoted transducer. Such a system can operate reliably without feedback. The present invention takes a somewhat similar approach, modified for transducer motion with two degrees of freedom.

U.S. Pat. Nos. 5,454,371 and 5,842,473 disclose digital image reconstruction and display techniques whereby three-dimensional volumetric image data may be presented on a two-dimensional display surface, through use of three-dimensional linear coordinate transformations. However, the manner in which image reconstruction and display may be accomplished is outside the scope of the present invention.

A typical practical embodiment of the present invention provides a hand-held probe which carries therewithin an ultrasonic transducer, and is such as to accomplish volumetric ultrasound scanning of a target within a conical scanning field. In such a probe, in keeping with the present invention, a permanent magnet is affixed to the rear of a carriage containing the ultrasonic transducer. The carriage is mounted for tilt motion with at least two degrees of freedom about a central pivot point by means of a gimbal or similar mechanism. The carriage and pivot mechanism are disposed within a stator assembly containing at least two fixed, hemispheric electromagnet coils. The whole is contained within a probe housing having an acoustically transparent window at the end closest to the transducer, through which the emitted and received sound pluses travel.

In operation, the electromagnet coils are energized with appropriately phased alternating electric currents, in order to cause the carriage assembly to rotate about the central pivot point. The speed of rotation is set by the frequency of the drive current; the amount by which the rotation axis tilts outward from the central axis is set by the drive current amplitude. Periodic variation of the drive current amplitude causes periodic variation of the tilt angle, in effect causing in-and-out spiral motion of the transducer.

The electromagnet coils are energized by means of a digital electronic switching system, resulting in highly repeatable motion of the transducer. In applications where continuous feedback control based on direct sensing of the transducer's position is not practical (e.g., when practical size constraints of an ultrasonic imaging probe do not permit inclusion of sensor components), the motion may be calibrated once using external feedback devices, and will remain stable long enough to permit accurate images to be acquired. Thus a three-dimensional ultrasound tomographic imaging system may be implemented with a minimum of components and a very small and simple probe having but one moving part.

This basic design admits a number of useful variations, including without limitation the following:

1. Instead of disposing the transducer within a moving carriage, the carriage may instead contain an acoustic reflector to reflect and sweep the sound beam emitted by a fixed ultrasonic transducer.
2. The ultrasonic transducer may be replaced by another energy source and/or detector. In particular, an optical source such as a semiconductor diode laser or superluminescent diode, or one end of a flexible optical fiber coupled to a fixed energy source and/or detector at the far end of the fiber.
3. Although in ultrasonic imaging it is most common to utilize a single transducer for emission and detection of sound, in optical imaging either the source or detector device may be fixed. For example, with respect to variation #2 above, the light beam from a semiconductor diode type light source could be swept across the target area while reflections are received by a fixed, wide-field detector such as a photomultiplier tube.

SUMMARY OF THE INVENTION

The present invention provides a scanning device for scanning a target within a conical scanning field, using a moveable body from which scanning energy may be transmitted linearly outwardly toward a target, and from which signals which are indicative of reflected scanning energy which is reflected from a target in the conical scanning field, may be derived for further storage or display. The scanning device comprises:

A housing for the scanning device, which housing has a longitudinal axis.

A moveable body having a generally planar front surface from which scanning energy is transmitted linearly outwardly, and towards which reflected scanning energy is directed.

A permanent magnet which is physically associated with the moveable body so as to be moveable therewith.

The moveable body and permanent magnet are mounted within the housing in such a manner that they are jointly moveable with a tilt motion about a centre of rotation, with at least two degrees of freedom of movement about two axis of rotation which are perpendicularly disposed one to the other. The centre of rotation is located on the longitudinal axis of the housing; and the two perpendicularly disposed axis of rotation intersect at the centre of rotation, and are each perpendicular to the longitudinal axis of the housing.

At least two electromagnets having wound electromagnet coils form a hemispheric electromagnet coil assembly.

There is an electric drive means for energizing the wound electromagnet coils in cyclic fashion, by applying an alternating current signal to each individual wound electromagnet coil, where the signal applied to each wound electromagnet coil has a differing phase than the signal applied to any other wound electromagnet coil.

The alternating current signal which is applied to each of the wound electromagnet coils is out of phase with the alternating current signal applied to any other wound electromagnetic coil; and the phase relationship among the respective alternating current signals is 180°/n, where n is the number of wound electromagnet coils in the hemispheric electromagnet coil assembly.

Thus, when scanning energy is transmitted linearly away from the moveable body, and the hemispheric electromagnet coil assembly is energized by the electric drive means, a conical scanning field is swept.

The present invention further provides for either or both of the magnitude or frequency of the alternating current signal applied to each of the wound electromagnet coils to be periodically modulated so as to cause the conical path swept by the transmitted scanning energy to alternately narrow and widen. Thus, a target in the conical scanning field of the scanning device is volumetrically scanned.

In many practical embodiments of the present invention, the moveable body is an ultrasonic transducer which is mounted at a first end of a moveable carriage, and the permanent magnet is mounted at an opposed second end of the moveable carriage.

In other practical embodiments of the present invention, the moveable body is a mirror, and a source of scanning energy is directed towards the mirror in a manner so as to be re-transmitted linearly away therefrom.

In any embodiment of the present invention, the moveable body and the permanent magnet may be gimbal mounted within the housing.

In such instances, it is possible that the gimbal may have knife-edge bearings.

In other embodiments of the present invention, the moveable body and the permanent magnet may be mounted on an elastomeric membrane which is secured within the housing.

In a further embodiment of the present invention, an annular permanent magnet is mounted in the housing outwardly of the hemispheric electromagnet coil assembly. The annular permanent magnet has a polarity opposite to that of the permanent magnet mounted together with the moveable body, so as to repel the permanent magnet away therefrom and towards the longitudinal axis of the housing.

Another embodiment of the present invention contemplates a further solenoid electromagnet located on the longitudinal axis of the housing at the side of the hemispheric electromagnet coil assembly which is remote from the permanent magnet. A source of direct current electricity is connected to the solenoid electric magnet. The solenoid electromagnet may be momentarily energized by the source of direct current electricity so as to either attract or repel the permanent magnet.

The scanning device of the present invention may be employed in an ultrasonic scanner together with signal handling means for processing signals which are indicative of the scanning energy which is relucted from a target in the conical scanning field, so as to derive an image therefrom. Display means may be provided for displaying that image.

When the scanning device of the present invention includes an ultrasonic transducer, there may be an acoustic window which encloses the first end of the housing, and enclosure means enclosing an opposed second end of the housing, so that all of the ultrasonic transducer, the permanent magnet, and the hemispheric electromagnet coil assembly, are contained within the housing together with an ultrasonic sound conducting fluid.

In another embodiment of ultrasonic scanning device of the present invention, the ultrasonic transducer and the permanent magnet are enclosed within a capsule having an acoustic window at a first end thereof which is remote from the permanent magnet, together with an ultrasonic conducting fluid.

In still another embodiment of ultrasonic scanning device in keeping with the present invention, there is an acoustic window located at the end of the housing proximate the ultrasonic transducer, and a pliant and sealed acoustically transparent container of ultrasonic conducting fluid is mounted between the ultrasonic transducer and the acoustic window in acoustically conductive relation therewith.

A further embodiment of ultrasonic scanning device of the present invention contemplates a pliant and sealed acoustically transparent container of ultrasonic conducting fluid which is mounted in acoustically conductive relation with the ultrasonic transducer.

Still further, an ultrasonic scanning device in keeping with the present invention may comprise an acoustic window which is located at the end of the housing approximately ultrasonic transducer, and a pliant and highly elastic self-contained ball which may be an acoustically transparent elastomer, or gelatin, is mounted between the ultrasonic transducer and the acoustic window in acoustically conductive relation therewith.

Yet another embodiment of an ultrasonic scanning device of the present invention comprises a pliant and highly elastic self-contained ball which may be acoustically transparent elastomer or gelatin, and which is mounted in acoustically conductive relation with the ultrasonic transducer.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which:

FIG. 1 is a cutaway diagrammatic representation of a first embodiment of an ultrasonic scanner mechanism in keeping with the present invention;

FIG. 2 is a central vertical cross-section of the scanner of FIG. 1, taken in the direction of arrows 2—2;

FIG. 3 is a diagrammatic and perspective view of the scanning device of FIG. 1;

FIG. 4 shows a cutaway view similar to FIG. 3;

DETAILED DESCRIPTION OF THE PREFERRED EMBODIMENTS

Figure 5:
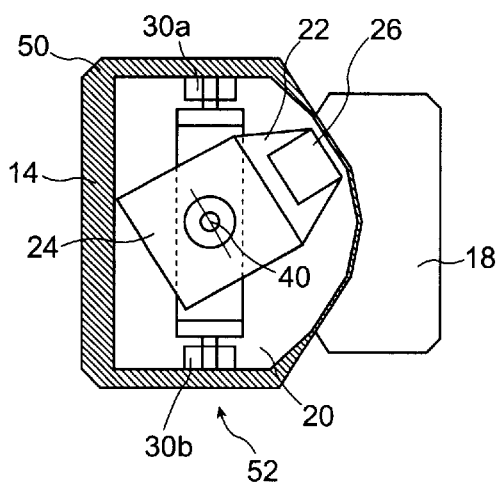
FIG. 5 shows a second embodiment of a scanning device in keeping with the present invention.

The novel features which are believed to be characteristic of the present invention, as to its structure, organization, use and method of operation, together with further objectives and advantages thereof, will be better understood from the following discussion.

Turning first to FIGS. 1 to 4, a typical ultrasonic scanning device in keeping with the present invention is illustrated and shown at 10. For clarity, the housing and acoustic window have been omitted from FIGS. 3 and 4.

The fixed components of the ultrasonic scanning device of FIGS. 1 through 4—and other embodiments, as will be evident from discussion hereafter—include a housing 12, an acoustic window 14, a stator assembly 16, and a hemispheric electromagnet coil assembly 18. The interior of the housing 12 is filled with a sound-conducting or ultrasonic-conducting fluid 20—typically, Dow Corning Corp. number 704 diffusion pump oil). The ultrasonic conducting fluid 20 also serves as a lubricant.

There is a moveable carriage 22 mounted in the housing, and on the moveable carriage 22 there is an ultrasonic transducer 24 and a permanent magnet 26. They are mounted to the stator assembly 16 by means of a gimbal mount 28. Typically, a gimbal 28 may be mounted having pairs of bearings 30a, 30b, and 32a, 32b. The bearings 30a, 30b, 32a, 32b permit the moveable carriage 22 to rotate about generally vertical and horizontal axis, respectively, as seen in FIGS. 1 and 2 in particular.

It will be noted that a closure member 34 is found at the end of the housing 12 opposite the acoustic window 14, so as to seal in the ultrasonic conducting fluid 20. However, the housing 12 must be sealed in such a manner that egress of wire connections (not shown) to the hemispheric electromagnet coil assembly 18 and to the ultrasonic transducer 24, is permitted.

The carriage 22 is symmetrical about a central axis 36, which may be also considered to be the axis for the transducer 24. It will also be noted that the housing 12 has its own longitudinal axis 38.

The transducer 24 and the permanent magnet 26 are generally cylindrical, and they are disposed within the carriage 22 so as also to be symmetric about the transducer axis 36.

It will also be noted, particularly from FIG. 1, that the transducer axis 36, the longitudinal axis 38 of the housing 12, and the axes of rotation of the gimbal bearing pairs 30a, 30b, and 32a, 32b, all intersect at a single point 40. That single point 40 is the centre of rotation for the moveable carriage 22, and more particularly for the combination of the transducer 24 and permanent magnet 26.

For purposes of this discussion, the transducer 24 might also be considered to be a moveable body, because in other embodiments of the present invention as are described hereafter, the transducer may be replaced with a generally planar mirror. In any event, the moveable body has a generally planar front surface from which scanning energy is transmitted linearly outwardly and towards which reflective scanning energy is directed from the target in the conical scanning field. Moreover, the permanent magnet 26 is physically associated with the moveable body so as to be moveable therewith—such as by being mounted on the carriage 22 or otherwise as described hereafter.

The moveable body and the permanent magnet are thereby mounted within the housing 12 in such a manner that they are jointly moveable with a tilt motion about the centre of rotation 40, with at least two degrees of freedom of movement about two axes of rotation which are perpendicularly disposed one to the other—the axes of rotation defined by the gimbal bearing pairs 30a, 30b, and 32a, 32b. The centre of rotation 40 is located on the longitudinal axis 38 of the housing 12, and the two perpendicularly disposed gimbal axes of rotation also intersect at the centre of rotation 40 and are each perpendicular to the longitudinal axis 38 of the housing 12.

The permanent magnet 26 is magnetized in the direction of the transducer axis 36. The coils which form the hemispheric electromagnet coil assembly 18 are wound in such a manner as to develop magnetic fields which are generally perpendicular to the probe axis which is the longitudinal axis 38 of the housing 12. In the simplest case, there are two coils whose windings are at right angles and which, when energized with electric current, develop magnetic fields which are generally parallel to the axes of rotation of the gimbal bearing pairs 30a, 30b, or 32a, 32b. More generally, there may be three or more coils, which are oriented so as to develop magnetic fields at equally spaced angular intervals about the longitudinal axis 38 of the housing 12.

The individual magnetic fields which are developed by the various coil windings add vectorially to yield a resultant magnetic field which is generally perpendicular to the probe axis 38—the longitudinal axis of the housing 12. In any such magnetic field which does not vary with time, the permanent magnet 26 is subject to a torque which serves to align its magnetic field with the resultant field developed by the coils, to the extent permitted by the freedom to move of the permanent magnet 26 as it is constrained by the gimbal mount 28. In general, the torque causes the permanent magnet 26, and with it the carriage 22 and the transducer 24, to tilt outwardly. That is, the transducer axis 36 tilts away from the probe axis 38 in the direction of the resultant magnetic field sector developed by the hemispheric electromagnet coil assembly 18.

According to the present invention, the windings of the hemispheric electromagnet coil assembly 18 are energized with sinusoidal alternating current signals which have generally equal amplitude and frequency, but which differ in phase by amounts corresponding to the relative angular orientation of the windings. For example, in the simplest case where there are two windings at right angles, there are two current signals which differ in phase by 90°. For three windings, there are three current signals at 0, 60°, and 120° relative phase, and so on. In each case, the number of signals equals the number of windings, and the relative phase difference in degrees is equal to the relative angular orientation of the windings.

Put in other words, the phase relationship among the respective alternating current signals is 180°/n, where n is the number of wound electromagnet coils in the hemispheric electromagnet coil assembly 18.

The effect of such polyphase sinusoidal excitation of the coil linings is such as to establish a resultant magnetic field which is generally perpendicular to the transducer axis 36. This resultant magnetic field revolves smoothly and continuously about the axis 36 at the frequency of the sinusoidal excitation signals. The permanent magnet 36 responds to the rotating magnetic field also by rotating about the probe axis 38. The angle between the transducer axis 36 and the probe axis 38 is directly proportional to the magnitude of the excitation current and inversely proportional to the square of the frequency. The underlying physics of that movement is the same as for a conical pendulum.

Once the permanent magnet 36, the carriage 22, and the transducer 24 are set in motion as described above, there is inertia; and the magnetic field established by being driven by out-of-phase signals as noted above will serve to keep pulling the whirling permanent magnet 36 back inwardly towards the probe axis 38. Thus, there is a centripetal force vector which is established, as noted above.

The overall effect is that the sound beam which is emitted from the generally planar front face of the ultrasonic transducer 24, and which is received by the transducer 24, sweeps out a conical surface, which is symmetric about the probe axis 38 and with its apex at the centre of rotation 40.

By introducing periodic variation or modulation of the magnitude of the coil excitation current, or the frequency of the coil excitation current, or both, the conical path of the sound beam emanating from the ultrasonic transducer 12 can be made to alternately narrow and widen in an in-and-out spiral motion. Appropriate choice of the modulation pattern which is determined during calibration of the scanning device before its use will permit the sound beam to sweep out a solid conical volume which is symmetric about the probe axis 38, with the apex at the centre of rotation 40. This provides a basis for volumetric scanning of a target which is located within the swept conical volume.

Formation of a stable, geometrically accurate image requires precise synchronization between pulse excitation of the transducer 24 and its motion, in order that the spatial orientation of each acquired image line may be precisely known. Preferably, this is achieved by a microprocessor digital control circuit which generates excitation current signals for the coil windings—for example, through digital/analog waveform synthesis techniques which are well established. The digital control circuit will also issue pulses to trigger excitation of the transducer, and other pulse signals for synchronization of the image formation and display means. These matters are now discussed, with reference to FIG. 14.

Figure 14:
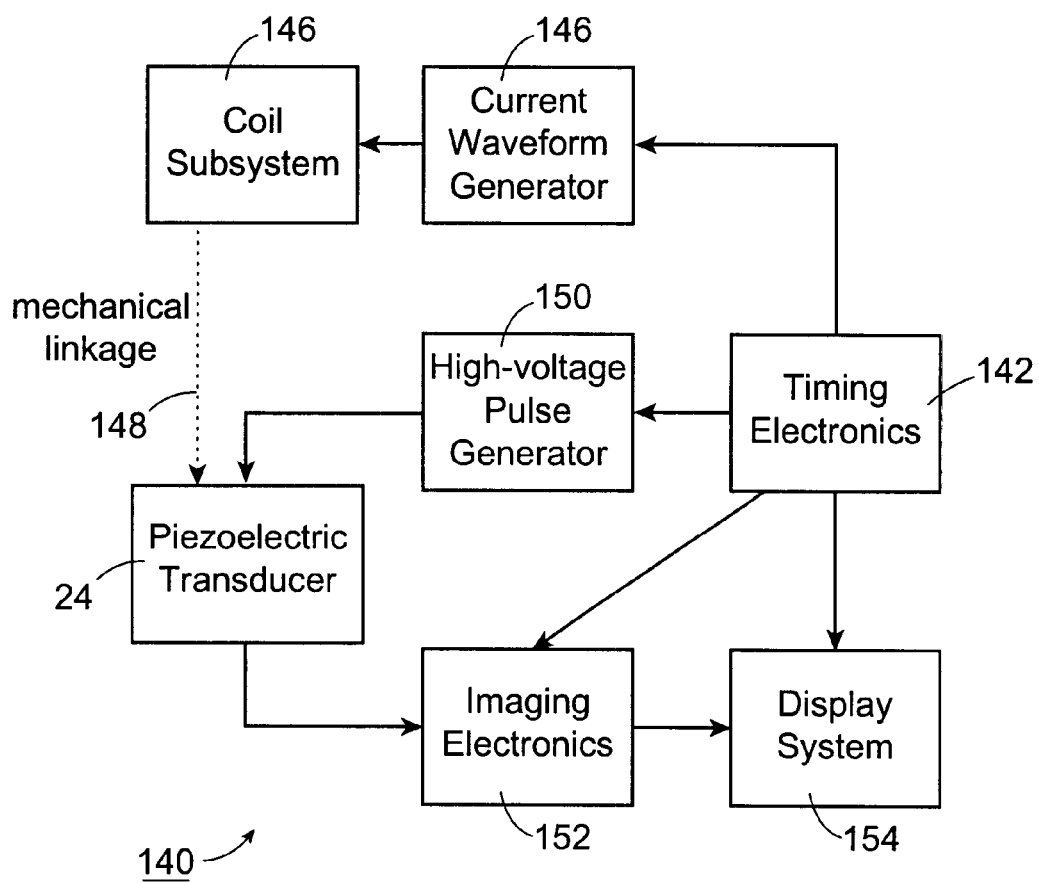
FIG. 14 provides a block diagram for the electronic control circuits to drive scanning devices in keeping with the present invention.

FIG. 14 sets out an electronic control circuit for controlling a scanning device such as that which has been described above with respect to FIGS. 1 to 4, or any other scanning device of the present invention as described hereafter. The particular issue is that means are provided to drive the hemispheric electromagnet coil assembly and to permit capture of meaningful signals as they are reflected back from the target.

The circuit 140 includes a timing electronics block 142, whose purpose is to supply timing signals to the other subsystems in the circuit. Typically, the timing electronics block comprises a set of phase-locked digital oscillators.

A current waveform generator 144 is a polyphase sine wave digital oscillator—although an analog oscillator might be used—which generates current waveforms to drive the deflection coils of the hemispheric electromagnet coil assembly 18, in order to move the transducer 26 through a spiral trajectory as noted above. The coil subsystem is shown at 146, and is linked through a mechanical linkage 148—which typically comprises the carriage 22, but which might comprise other mechanical linkage means as described hereafter—to the transducer 24.

The current waveform generator 144 also includes a high-current programable-gain output amplifier which actually drives the coil subsystem 146—the coils of hemispheric electromagnet coil assembly 18. If the output amplitude of the current reform generator 144 were to be held constant, polyphase excitation would cause the transducer 44 to precess in a circular motion. However, periodically increasing and decreasing the output amplitude, by means of the programable-gain amplifiers in the current waveform generator 144, will cause the path of the transducer 24 to spiral outwardly and inwardly, respectively. Preferably, the current waveform generator 144 provides polyphase sinusoidal output currents whose amplitudes vary periodically according to a triangle wave modulation function. Typical frequencies for the sinusoid are several hundred cycles per second, and for modulation about one cycle per second.

As the direction of scanning of the scanning energy transmitted from the transducer 24 is swept through its programmed—for example, spiral—trajectory, a high voltage pulse generator 150 emits excitation pulses which cause the transducer 24 to emit pulses of ultrasound, and thus to interrogate the target volume. The transducer 24 also receives the resultant ultrasonic echo trains, which are then processed via an imaging subsystem 152 in order to create images on a display system 154. Typically, the display system 154 is a CRT, a liquid crystal panel, gas-plasma matrix display, or other colour image display device.

The specific details of the imaging subsystem and the display system are beyond the scope of the present invention. However, it can be noted that a principal difficulty to be overcome is the matter of re-sampling the acquired image, which is most naturally defined on a spherical-coordinate grid, so as to render it amenable to presentation on a standard image display device such as a cathode ray tube or other display device as noted above. Previous methods are shown in U.S. Pat. No. 5,454,371 and laid open Canadian Patent application Ser. No. 2,254,939.

As noted above, in the first embodiment of the present invention as it has been discussed with respect to FIGS. 1 to 4, the housing 12 is entirely filled with the acoustic coupling fluid 20. It is sealed at its rear end by a closure 34, and at its front end with an acoustic window 14—material which is at least acoustically transparent. The electrical connections to the transducer 24 and to the hemispheric electromagnetic coil assembly 18 are made through suitably fluid-sealed openings in the housing 12—typically through the closure 34, and are not shown.

It should also be noted that the acoustic coupling fluid 20 not only serves as a lubricant for the gimbal bearings 30a, 30b, and 32a, 32b, it also assists with the conduction of waste heat away from the coil assemblies of the hemispheric electromagnetic coil assembly 18.

Of course, if necessary, it is possible to provide suitable circulation means to permit continuous circulation of the acoustic coupling fluid 20 into and out of the assembly of FIGS. 1 through 4, and through a heat exchanger or refrigeration system.

Applicant now turns to a discussion of FIGS. 5 through 12, in particular, in which the same reference numerals are used for the same or like elements as they appear in those figures of drawings. In each of those figures of drawings, for purposes of simplification, an indication of the housing and stator assembly has been eliminated where appropriate.

Referring to a second embodiment of the present invention as illustrated in FIG. 5, it is seen that the material of the acoustic window 14 is extended as shown at 50 so as to form a closed capsule 52 which is filled with the acoustic coupling fluid or ultrasonic conducting fluid 20. Obviously, an electrical connection to the transducer 24 is made through a suitably fluid-sealed hole in the capsule 52, not shown. This arrangement avoids overheating of the acoustic coupling fluid 20, and permits the hemispheric electromagnet coil assembly 18 to be cooled through the circulation of air or some other fluid coolant as required. The arrangement shown in FIG. 5 also facilitates the optional replacement of the sealed capsule 52, together with its contents, if necessary.

Figure 6:
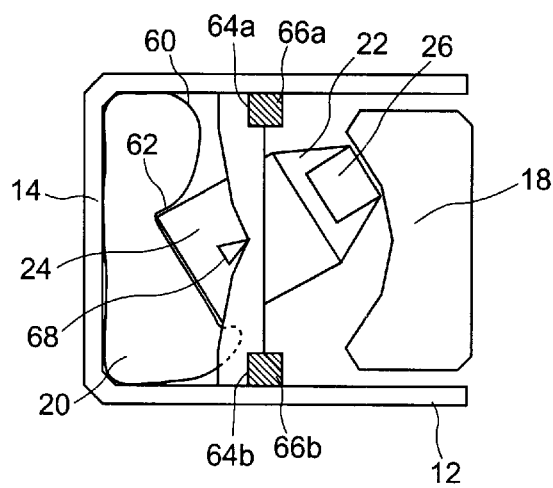
FIG. 6 shows a third embodiment of a scanning device in keeping with the present invention.

Turning now to FIG. 6, a third embodiment is shown, wherein the acoustic coupling fluid 20 is confined within a balloon-like sealed bag or other acoustically transparent container 60. The outer skin of the container 60 is, itself, acoustically transparent, and is an elastic membrane which is attached at the sides of the transducer 24 in the region 62. Acoustic coupling between the front of the fluid bag 60 and the acoustic window 14 may be effected by applying a thin film of acoustically conductive gel or glue during assembly of the embodiment shown in FIG. 6.

The elasticity of the fluid bag 60 provides continuous rearward pressure on the transducer 26, thereby permitting use of knife-edge bearings 64a, 64b which bear against blocks 66a and 66b, respectively, together with a further pair of knife-edge bearings 68 in the transverse direction, all of which mount the modified gimbal 70. The fact that the knife-edge bearings 64a, 64b, 68 are not immersed in the acoustic coupling fluid 20 permits use of the knife-edge pairs as electrical connections to the transducer 24, thereby obviating the need for a separate wire. Preferably, the gimbal mounting 70 is formed of electrically insulating material having, for example, electro-deposited metal contacts thereon. Also, preferably, the knife-edge bearings 64a, 64b, 68 are mercury-wetted to ensure constant, low resistance electrical connection.

Figure 7:
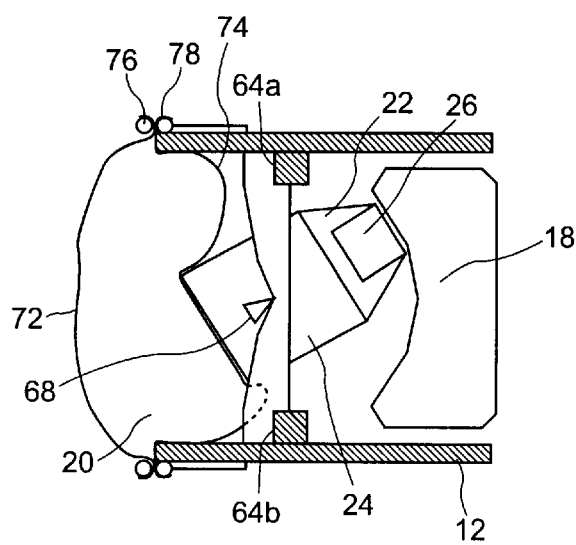
FIG. 7 shows a fourth embodiment of a scanning device in keeping with the present invention.

FIG. 7 shows a fourth embodiment which is not dissimilar in many respects to the embodiment of FIG. 6. However, the embodiment of FIG. 7 is particularly applicable and useful for ocular scanning. Here, however, the rigid acoustic window 14 shown in FIG. 6 is replaced by a second elastic membrane 72 which is opposed to an elastic membrane 74 that is attached to the sides of the transducer 24. The membranes 72 and 74 are secured in place such as by means of retaining rings 76, 78, respectively. Those retaining rings 76, 78 also serve to position the expanded fluid bag which is formed by the membrane 72 and 74 and which contains the acoustic coupling fluid 20, with respect to the circular front opening of the housing 12. Good acoustic coupling between the rear membrane 74 and the transducer 24 may be facilitated by applying a thin film of acoustically conductive gel, oil, or other fluid during assembly.

The arrangement which is illustrated in FIG. 7 provides a soft, convex front surface for the ultrasonic probe assembly. This facilitates good acoustic coupling when pressed against the convex surface of the front of the eye, while also distributing the applied pressure over the maximum possible area and hence reducing compression of the eye. A probe of the type shown in FIG. 7 may safely be applied directly to the cornea or sclera of an open eye, rather than to the closed eyelid as is the most prevalent technique for contact ocular ultrasound. In most cases, naturally occurring tears, or a single drop of water or saline solution, should provide ample acoustic coupling to the eye.

Several other advantages come from the embodiment of FIG. 7. The first is that the fluid bag which is formed by the membrane 72 and 74, containing the acoustic coupling fluid 20, is readily detachable. The natural tendency of the elastic membrane 74 to form a convex rear surface facilitates re-attachment to the housing 12. Of course, as noted above, when a fluid bag as shown in FIG. 7 is being reattached, preferably the front surface of the transducer 24 is first prepared by the application of a single drop of acoustically conductive gel or other fluid medium. The natural convexity of the membrane 74, when applied to the front face of the transducer 24 and pressed thereagainst, will serve to squeeze out air bubbles which are at the interface.

Further, the embodiment of FIG. 7 permits for a detachable bag that may be sterilized or disposed of. This arrangement clearly allows for all necessary antiseptic steps to be taken, and the assurance that either sterilized or new equipment is brought into physical contact with each patient, in turn.

Figure 8:
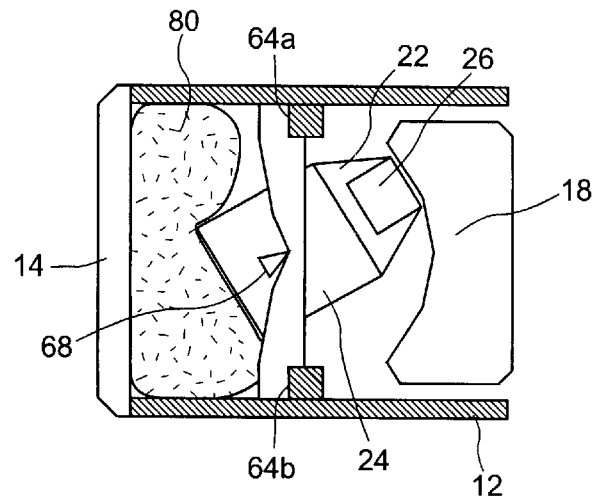
FIG. 8 shows a fifth embodiment of a scanning device in keeping with the present invention.

Turning now to FIG. 8, a fifth embodiment is shown which is similar to that of FIG. 6. However, in this embodiment, the fluid-filled elastomeric bag 60 is replaced by a solid ball which is pliant and highly elastic, a self-contained ball 80. The ball 80 may be gelatin, or it may be an acoustically transparent elastomer of the sort which is sold by Radiation Measurements, Inc., of Middleton, Wis., in association with the trade-mark SOLID WATER. Acoustic coupling between the transducer 24 and the pliant and highly elastic self-contained ball 80, and the acoustic window 14, is effected by applying a thin film of acoustically conductive gel during assembly.

Figure 9:
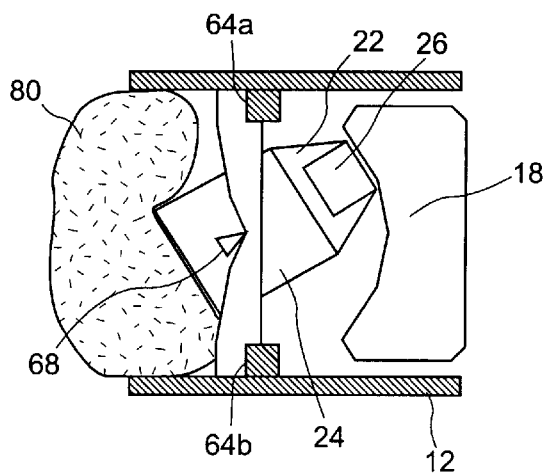
FIG. 9 shows a sixth embodiment of a scanning device in keeping with the present invention.

FIG. 9 shows a sixth embodiment which is similar to FIG. 8 in that it employs a pliant, highly elastic, self-contained ball 80. However, the embodiment of FIG. 9 employs no acoustic window, and thus is similar in many respects to that of FIG. 7. Clearly, just as was discussed with respect to the embodiment of FIG. 7, the embodiment of FIG. 9 permits replacement of the ball 80 and sterilization or, more preferably, disposal of a used ball 80 and replacement with another one.

Figure 10:
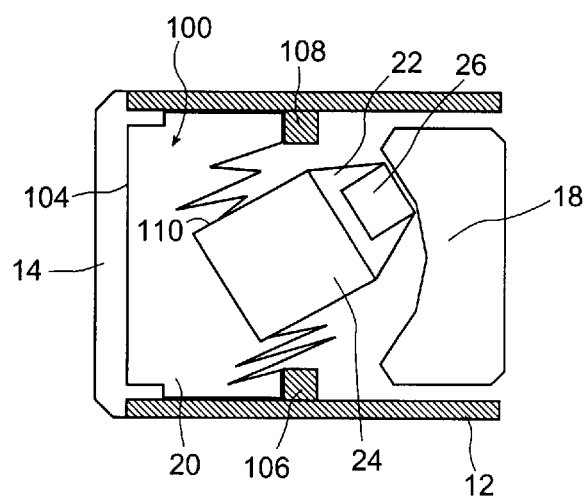
FIG. 10 shows a seventh embodiment of a scanning device in keeping with the present invention.

The embodiment of FIG. 10 derives in many respects from the embodiment of FIG. 6. Here, however, the gimbal mounting 70 and the fluid-filled container 60 are replaced by another fluid-filled container 100 which comprises a circularly symmetric elastomer membrane 102 and a further membrane 104 within which the acoustic coupling fluid 20 is maintained. In this case, however, the elastomeric membrane 102 is secured within the housing 12 at 106, against a ring 108, and is secured to the transducer 24 at 110. The physical characteristics of the elastomeric membrane 102 are such that motion of the transducer 24 and permanent magnet 26 on the carriage 22 emulates that of the previous embodiments where the transducer 24 and permanent magnet 26 are gimbal mounted within the housing 12.

Figure 11:
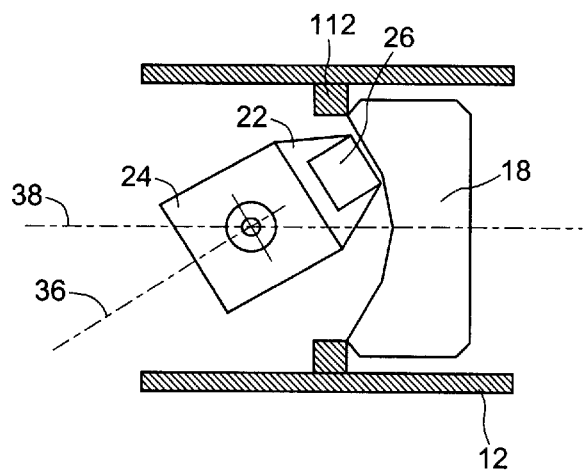
FIG. 11 shows the incorporation of an annular magnet in any embodiment of the present invention.

FIG. 11 shows a further enhancement to any previous embodiment of the present invention. As such, the precise mounting for the transducer 24 and permanent magnet 26 are not shown—partly for purposes of clarity, and partly so as to ensure that it is clearly understood that the enhancement shown in FIG. 11—and, for that matter, in FIG. 12 which is discussed hereafter—is independent of the manner in which the moveable body which comprises the transducer 24 and the permanent magnet 26 may be mounted, and is independent of other features surrounding various alternatives for placement of a coupling, acoustically transparent fluid.

Here, a ring shaped or annular permanent magnet 112 is mounted within the housing 12, and is oriented so as to repel the rear end of the permanent magnet 26 which is mounted on the carriage 22. This configuration enables reciprocating motion of the moveable carriage 22 or moveable body comprising the transducer 24 and permanent magnet 26, for conventional two-dimensional scanning, as follows:

The windings of the hemispheric electromagnet coil assembly 18 are energized with alternating current signals which are either fully in-phase or fully out-of-phase, and whose relative amplitudes are chosen so as to set up a periodically reversing magnetic field at a fixed orientation perpendicular to the probe axis 38. The alternating current signals do not have to be sinusoidal in this specific application for two-dimensional scanning; they might be square wave, for example. Local repulsive forces between the permanent magnets 112 and 26 will cause the permanent magnet 26 and the carriage 22 to be repelled away from the annular permanent magnet 112 in a direction towards the longitudinal axis of the housing 12—the probe axis 38. The use of rebound permanent magnets, but in another sense, is also described in U.S. Patent No. "unknown" (to issue from Ser. No. 09/409,095).

With the coils energized as described above, the configuration shown in FIG. 11 will provide a two-dimensional sector scanning with an arbitrary scanning plane which is perpendicular to the probe axis 38. Here, however, the scanning plane may be selected entirely by electronic means by adjusting the relative amplitude and phase of the coil current signals as they are issued from the current waveform generator 144. This is done while the probe itself—that is, the housing 12 and the associated components—remain fixed relative to the target being scanned. This capability is useful when it may be difficult, impossible, or undesirable to physically rotate the housing 12 relative to the target. For example, when the probe is an endocavity type of probe which is located at the end of a catheter which is inserted at some depth into living tissue, or in image-assisted surgery applications where it is desirable to physically clamp the probe housing 12 into a fixed position relative to the target tissue.

Figure 12:
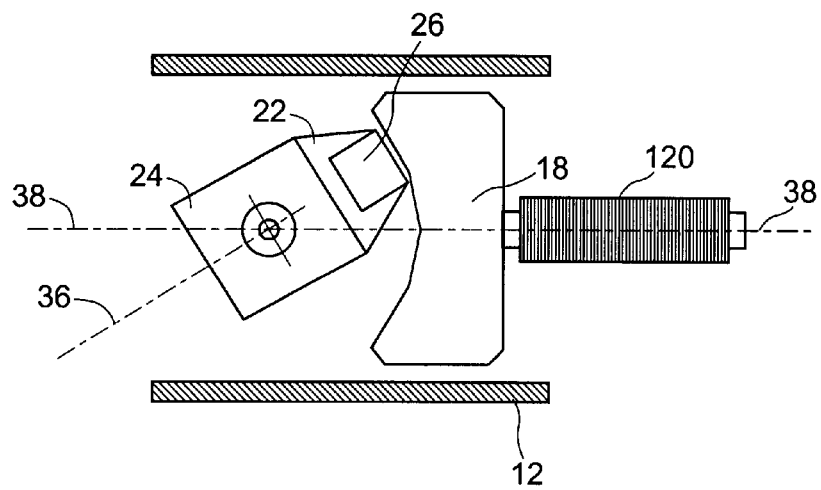
FIG. 12 shows the incorporation of a solenoid electromagnet in any embodiment of the present invention.

FIG. 12 illustrates yet a further enhancement to the present invention, where a simple solenoid electromagnet 120 is located on the longitudinal axis 38 of the housing 12 at the side of the hemispheric electromagnet coil assembly 18 which is remote from the permanent magnet 26. The solenoid electromagnet 120 is connected to a source of direct current electricity (not shown). It will be clear that when the solenoid electromagnet 120 is energized with direct current, it will either attract or repel the permanent magnet 26. When energized for attraction, the solenoid electromagnet 120 will tend to bring the transducer axis 36 into alignment with the probe axis 38. When the solenoid electromagnet 120 is energized for repulsion of the permanent magnet 26, it will tend to force the transducer axis 36 away from the probe axis 38. Either case may facilitate proper starting of a spiral scanning motion, depending upon the specifics of the electronic means by which the coil drive signals are generated for the hemispheric electromagnet coil assembly 18. Moreover, it should be noted, that if the hemispheric electromagnet coil assembly 18 is not energized at all, and the solenoid electromagnet 120 is energized so as to attract the permanent magnet 26 and thus align the transducer axis 36 with the probe axis 38, the probe assembly may be readily used for amplitude mode (A-mode) scanning.

It follows that a probe which is built having both the annular permanent magnet 112 of FIG. 11 and the solenoid electromagnet 120 of FIG. 12, together with appropriate electronic means to permit either polyphase sinusoidal or fixed-phase square excitation, or no excitation, of the hemispheric electromagnet coil assembly 18, will provide for a multi-mode probe which is capable of A-mode, planar B-mode, and spiral three-dimensional B-mode imaging.

Clearly, the embodiments that have been described above can be adapted for scanning modalities other than ultrasound, if the transducer 24 is replaced by some other source or detector of directed energy. For example, a laser or superluminescent diode, or an optical fibre conducting light to and/or from such a source or detector of directed energy may be employed.

As a further example, the ultrasonic transducer may be replaced with a mirror, and a source of scanning energy is directed toward the mirror in a manner so that the scanning energy is re-transmitted linearly away from the mirror. The mirror and the permanent magnet are mounted on a moveable body such as the carriage 22 so as to be physically associated each with the other and to be moveable each with the other. It is evident that such an arrangement can be made, as necessary, in any of the embodiments so far described.

Figure 13:
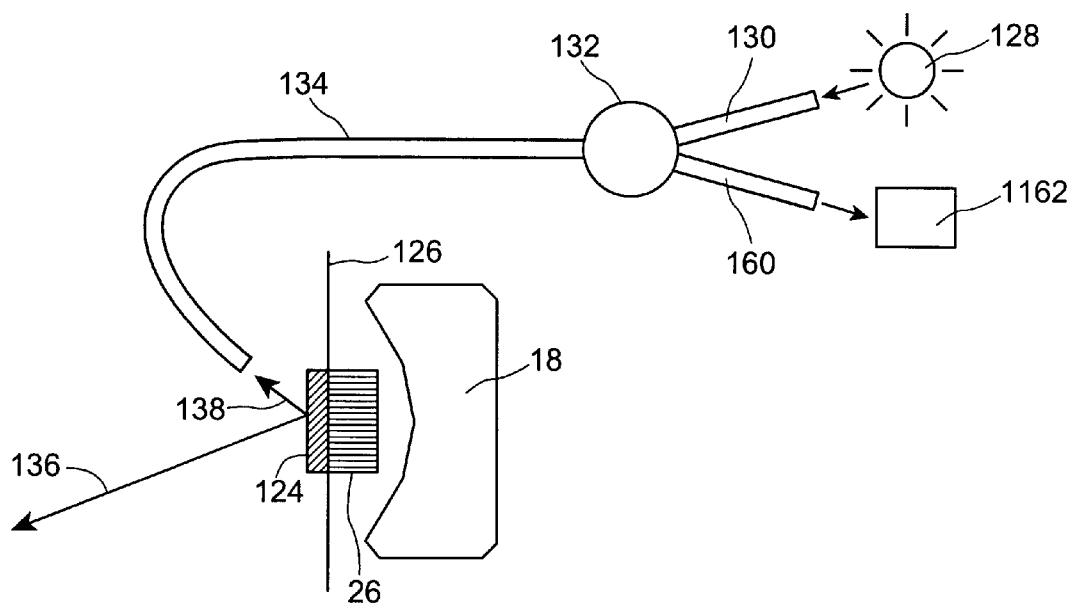
FIG. 13 diagrammatically illustrates the adoption of the present invention for use in optical scanning.

FIG. 13 provides an embodiment in which, in fact, a mirror 124 has been substituted for the transducer 24, and is moveable together with the permanent magnet 26 in the same manner as described above. However, in this configuration, an elastomer membrane 126 serves as the flexural bearing instead of a gimbal mounting. Once again, the geometry of the embodiment of FIG. 13 is such that a centre of rotation is located within the combined mirror 124 and permanent magnet 26, and the motion of the moveable body which comprises the mirror 124 and permanent body 26 is such that it has a tilt motion about the centre of rotation. Clearly, the geometry and characteristics of the elastomer membrane 126 are such as to permit at least two degrees of freedom of movement about two axes of rotation which are perpendicularly disposed one to the other.

Referring to FIG. 13, light from a source 128—which is preferably a superluminescent diode or other low coherence light source—is conducted by means of an optical fibre 130 through an optical coupler 132, and thence through an optical fibre 134 to the mirror 124. The light is thence transmitted outwardly as shown at 136 towards the target to be scanned. Light energy returning from the target travels along the reverse path, starting at 138, through the fibre 134 and optical coupler 132 to an optical fibre 160 and thence to an optical detector 162.

Obviously, energization of the hemispheric electromagnet coil assembly 18 is as described above, thereby providing for various scanning paths as noted previously.

It should also be noted that when a solenoid electromagnet of the sort described above with respect to FIG. 12 is employed in the arrangement of FIG. 13, then the mirror 124 can be made to advance forwardly or rearwardly along the probe axis 38. This provides the means for A-scanning in optical coherence tomography.

The specifics of the optical components are otherwise beyond the scope of the present invention, but are such as know to those skilled in the art, particularly that of optical coherence tomography.

There has been described various embodiments of scanning devices which are capable of scanning a conical scanning field, and with appropriate control are capable of making a volumetric scan within the conical scanning field. Typically, but not always, the scanning device is an ultrasonic device, but it may also be an optical device wherein a mirror replaces a transducer.

Obviously, an ultrasonic scanner may be built using any scanning device of the present invention, together with signal handling means for processing signals indicative of the scanning energy which is reflected from a target in the conical scanning field so as to derive an image therefrom and so as to display the image on suitable display means.

Other embodiments beyond those which have been described herein may be obvious to those skilled in the respective art, and may be used in the design and manufacture of the apparatus of the present invention without departing from the spirit and scope of the accompanying claims.

It should also be noted that the term "generally planar" as it used in the context of this application will be understood by persons skilled in the art to mean planar, or slightly concave. Very often, for purposes of focussing a beam of scanning energy, the front surface of a transducer or mirror may be slightly concave, or planar, as is well known.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

What is claimed is:

1. A scanning device for scanning a target within a conical scanning field, using a moveable body from which scanning energy may be transmitted linearly outwardly towards a target, and from which signals which are indicative of reflected scanning energy which is reflected from a target in said conical scanning field may be derived for further storage or display, said scanning device comprising:

a housing for said scanning device, said housing having a longitudinal axis;

a moveable body having a generally planar front surface from which scanning energy is transmitted linearly outwardly and towards which reflected scanning energy is directed;

a permanent magnet physically associated with said moveable body so as to be movable therewith;

said moveable body and said permanent magnet being mounted within said housing in such a manner that they are jointly moveable with a tilt motion about a centre of rotation, with at least two degrees of freedom of movement about two axes of rotation which are perpendicularly disposed one to the other, wherein said centre of rotation is located on said longitudinal axis of said housing, and said two perpendicularly disposed axes of rotation intersect at said centre of rotation and are each perpendicular to said longitudinal axis of said housing;

at least two electromagnets having wound electromagnet coils which form a hemispheric electromagnet coil assembly; and electric drive means for energizing said wound electromagnet coils in cyclic fashion, by applying an alternating current signal to each individual wound electromagnet coil, where the signal applied to each respective wound electromagnet coil has a differing phase than the signal applied to any other wound electromagnet coil;

wherein the alternating current signal applied to each of said wound electromagnet coils is out of phase with the alternating current signal applied to any other wound electromagnet coil;

wherein the phase relationship among the respective alternating current signals is 180°/n, where n is the number of wound electromagnet coils in said hemispheric electromagnet coil assembly;

wherein when scanning energy is transmitted linearly away from said moveable body, and said hemispheric electromagnet coil assembly is energized by said electric drive means, a conical scanning field is swept; and wherein said movable body is an ultrasonic transducer mounted at a first end of a movable carriage, and said permanent magnet is mounted at an opposed second end thereof.

2. The scanning device of claim 1, wherein at least one of the magnitude and frequency of the alternating current signal applied to each of said wound electromagnet coils is periodically modulated so as to cause the conical scanning field swept by said transmitted scanning energy to alternately narrow and widen, whereby a target in the conical scanning field of said scanning device is volumetrically scanned.

3. The scanning device of claim 1, wherein said moveable body and said permanent magnet are gimbal mounted within said housing.

4. The scanning device of claim 3, wherein said moveable body and said permanent magnet are mounted on a gimbal having knife-edge bearings.

5. The scanning device of claim 1, wherein said moveable body and said permanent magnet are mounted on an elastomeric membrane which is secured within said housing.

6. An ultrasonic scanner comprising the scanning device of claim 1 together with signal handling means for processing signals indicative of scanning energy reflected from a target in said conical scanning field so as to derive an image therefrom, and display means for displaying said image.

7. The scanning device of claim 1, wherein an acoustic window encloses a first end of said housing, and closure means encloses an opposed second end of said housing, and all of said ultrasonic transducer, said permanent magnet, and said hemispheric electromagnet coil assembly, are contained within said housing together with an ultrasonic sound conducting fluid.

8. The scanning device of claim 1, wherein said ultrasonic transducer and said permanent magnet are enclosed within a capsule having an acoustic window at a first end thereof remote from said permanent magnet, together with an ultrasonic conducting fluid.

9. The scanning device of claim 1, wherein an acoustic window is located at the end of said housing proximate said ultrasonic transducer, and a pliant and sealed acoustically transparent container of ultrasonic conducting fluid is mounted between said ultrasonic transducer and said acoustic window in acoustically conductive relation therewith.

10. The scanning device of claim 1, wherein a pliant and sealed acoustically transparent container of ultrasonic conducting fluid is mounted in acoustically conductive relation with said ultrasonic transducer.

11. The scanning device of claim 1, wherein an acoustic window is located at the end of said housing proximate said ultrasonic transducer, and a pliant and highly elastic self-contained ball chosen from the group consisting of an acoustically, transparent elastomer, and gelatin, is mounted between said ultrasonic transducer and said acoustic window in acoustically conductive relation therewith.

12. The scanning device of claim 1, wherein a pliant and highly elastic self-contained ball chosen from the group consisting of an acoustically transparent elastomer, and gelatin, is mounted in acoustically conductive relation with said ultrasonic transducer.

13. A scanning device for scanning a target within a conical scanning field, using a moveable body from which scanning energy may be transmitted linearly outwardly towards a target, and from which signals which are indicative of reflected scanning energy which is reflected from a target in said conical scanning field may be derived for further storage or display, said scanning device comprising:
   a housing for said scanning device, said housing having a longitudinal axis;
   a moveable body having a generally planar front surface from which scanning energy is transmitted linearly outwardly and towards which reflected scanning energy is directed;
   a permanent magnet physically associated with said moveable body so as to be movable therewith;
   said moveable body and said permanent magnet being mounted within said housing in such a manner that they are jointly moveable with a tilt motion about a centre of rotation, with at least two degrees of freedom of movement about two axes of rotation which are perpendicularly disposed one to the other, wherein said centre of rotation is located on said longitudinal axis of said housing, and said two perpendicularly disposed axes of rotation intersect at said centre of rotation and are each perpendicular to said longitudinal axis of said housing;
   at least two electromagnets having wound electromagnet coils which form a hemispheric electromagnet coil assembly; and
   electric drive means for energizing said wound electromagnet coils in cyclic fashion, by applying an alternating current signal to each individual wound electromagnet coil, where the signal applied to each respective wound electromagnet coil has a differing phase than the signal applied to any other wound electromagnet coil; and
   an annular permanent magnet mounted in said housing outwardly of said hemispheric electromagnet coil assembly, said annular permanent magnet having a polarity opposite to that of said permanent magnet mounted together with said moveable body as to repel said permanent magnet away therefrom and towards said longitudinal axis of said housing;
   wherein the alternating current signal applied to each of said wound electromagnet coils is out of phase with the alternating current signal applied to any other wound electromagnet coil;
   wherein the phase relationship among the respective alternating current signals is 180°/n, where n is the number of wound electromagnet coils in said hemispheric electromagnet coil assembly;
   wherein when scanning energy is transmitted linearly away from said moveable body, and said hemispheric electromagnet coil assembly is energized by said electric drive means, a conical scanning field is swept; and
   wherein said movable body is an ultrasonic transducer mounted at a first end of a movable carriage, and said permanent magnet is mounted at an opposed second end thereof.

14. A scanning device for scanning a target within a conical scanning field, using a moveable body from which scanning energy may be transmitted linearly outwardly towards a target, and from which signals which are indicative of reflected scanning energy which is reflected from a target in said conical scanning field may be derived for further storage or display, said scanning device comprising:
   a housing for said scanning device, said housing having a longitudinal axis;
   a moveable body having a generally planar front surface from which scanning energy is transmitted linearly outwardly and towards which reflected scanning energy is directed;
   a permanent magnet physically associated with said moveable body so as to be movable therewith;
   said moveable body and said permanent magnet being mounted within said housing in such a manner that they are jointly moveable with a tilt motion about a centre of rotation, with at least two degrees of freedom of movement about two axes of rotation which are perpendicularly disposed one to the other, wherein said centre of rotation is located on said longitudinal axis of said housing, and said two perpendicularly disposed axes of rotation intersect at said centre of rotation and are each perpendicular to said longitudinal axis of said housing;
   at least two electromagnets having wound electromagnet coils which form a hemispheric electromagnet coil assembly; and
   electric drive means for energizing said wound electromagnet coils in cyclic fashion, by applying an alternating current signal to each individual wound electromagnet coil, where the signal applied to each respective wound electromagnet coil has a differing phase than the signal applied to any other wound electromagnet coil; and
   a solenoid electromagnet located on said longitudinal axis of said housing at the side of said hemispheric electromagnet coil assembly remote from said permanent magnet and a source of direct current electricity connected to said solenoid electromagnet;
   whereby said solenoid electromagnet may be momentarily energized by said source of direct current electricity so as to either attract or repel said permanent magnet;
   wherein the alternating current signal applied to each of said wound electromagnet coils is out of phase with the alternating current signal applied to any other wound electromagnet coil;
   wherein the phase relationship among the respective alternating current signals is 180°/n, where n is the number of wound electromagnet coils in said hemispheric electromagnet coil assembly;

wherein when scanning energy is transmitted linearly away from said moveable body, and said hemispheric electromagnet coil assembly is energized by said electric drive means, a conical scanning field is swept; and wherein said movable body is an ultrasonic transducer mounted at a first end of a movable carriage, and said permanent magnet is mounted at an opposed second end thereof.

* * * * *